(12) United States Patent
Love

(10) Patent No.: US 6,573,290 B1
(45) Date of Patent: Jun. 3, 2003

(54) DFMO AND CELECOXIB IN COMBINATION FOR CANCER CHEMOPREVENTION AND THERAPY

(75) Inventor: Richard Love, San Antonio, TX (US)

(73) Assignee: ILEX Oncology, Inc., San Antonio, TX (US)

(*) Notice: Subject to any disclaimer, the term of this patent is extended or adjusted under 35 U.S.C. 154(b) by 0 days.

(21) Appl. No.: 09/573,089

(22) Filed: May 17, 2000

Related U.S. Application Data

(60) Provisional application No. 60/134,582, filed on May 17, 1999.

(51) Int. Cl.$^7$ ..................... A61K 31/415; A61K 31/195
(52) U.S. Cl. ........................................ 514/406; 514/564
(58) Field of Search ................................. 514/406, 564

(56) References Cited

U.S. PATENT DOCUMENTS

| | | | |
|---|---|---|---|
| 4,330,559 A | 5/1982 | Bey et al. | 424/319 |
| 4,413,141 A | 11/1983 | Bey et al. | 562/561 |
| 4,499,072 A | 2/1985 | Sunkara et al. | 424/85 |
| 4,859,452 A | 8/1989 | Ajani et al. | 424/10 |
| 4,925,835 A | 5/1990 | Heston | 514/183 |
| 5,002,879 A | 3/1991 | Bowlin et al. | 435/71.1 |
| 5,760,068 A * | 6/1998 | Talley et al. | 514/403 |
| 6,258,845 B1 * | 7/2001 | Gerner et al. | 514/544 |

FOREIGN PATENT DOCUMENTS

WO  WO 00/38730  7/2000

OTHER PUBLICATIONS

Marx et al., 1983, Surg. Forum, 34, 439–40 Abstract Only.*
Meyskens et al., 1992, Cancer Chemoprev., 541–55 Abstract Only.*
Carbone et al., "Phase I chemoprevention study of piroxicam and alpha–difluoromethylornithine." *Cancer Epidemiol Biomarkers Prev* 7: 907–912, 1998.
Gann et al., "Low–dose aspirin and incidence of colorectal tumors in a randomized trial," *J. Nat'l Cancer Inst.*, 85:1220–1224, 1993.
Giardiello et al., "Ornithine decarboxylase and polyamines in familial adenomatous polyposis," *Cancer Res.*, 57:199–201, 1997.
Giovannucci et al., "Aspirin use and the risk for colorectal cancer and adenomas in male health professionals," *Ann. Intern. Med.*, 121:241–246, 1994.
Greenberg et al., "Reduced risk of large–bowel adenomas among aspirin users," *J. Nat'l Cancer Inst.*, 85:912–916, 1993.
Jacoby et al., "Chemopreventive efficacy of combined piroxicam and difluoromethylornithine treatment of Apc mutant min mouse adenomas, and selective toxicity against Apc mutant embryos," *Cancer Res.*, 60:1864–1870, 2000.
Kawamori et al., "Chemopreventive activity of celecoxib, a specific cyclooxygenase–2 inhibitor, against colon carcinogenesis." *Cancer Res* 58: 409–412, 1998.
Kulkarni et al., "Effect of the chemopreventive agents piroxicam and D,L–α–difluoromethylornithine on intermediate biomarkers of colon carcinogenesis," *Carcinogenesis*, 13:995–1000, 1992.
Li et al., "Prevention by aspirin and its combination with α–difluoromethylornithine of azoxymethane–induced tumors, aberrant crypt foci and prostaglandin E2 levels in rat colon." *Carcinogenesis* 20: 425–30, 1999.
Luk and Baylin, "Onithine decarboxylase as a biological marker in familial colonic polyposis," *N. Eng. J. Med.*, 311:80–83, 1984.
McCann and Pegg, "Ornithine decarboxylase as an enzyme target for therapy," *Pharmacol. Ther.*, 54:195–215, 1992.
Meyskens and Gerner, "Development of difluoromethylornithine as a chemoprevention agent for the management of colon cancer," *J. Cell. Biochem.*, 22:126–131, 1995.
Muscat et al., "Nonsteroidal antiinflammatory drugs and colorectal cancer," *Cancer*, 74:1847–1854, 1994.
Pegg, "Polyamine metabolism and its importance in neoplastic growth and a target for chemotherapy," *Cancer Res.*, 48:759–774, 1988.
Reddy et al., "Chemoprevention of colon carcinogenesis by concurrent administration of piroxicam, a nonsteroidal anti–inflammatory drug with D,L–α–difluoromethylornithine, and ornithine decarboxylase inhibitor, in diet," *Cancer Res.*, 50:2562–2568, 1990.
Ritland and Gendler, "Chemoprevention of intestinal adenomas in the Apc$^{Min}$ mouse by piroxicam: kinetics, strain effects and resistance to chemosuppression." *Carcinogenesis* 20: 51–58, 1999.
Singh and Lippman, "Cancer chemoprevention—Part 1: retinoids and carotenoids and other classic antioxidants," *Oncology*, 12:1643–1660, 1998.
Tempero et al., "Chemoprevention of mouse colon tumors with difluromethylornithine during and after carcinogen treatment," *Cancer Res.*, 49:5793–5797, 1989.

* cited by examiner

Primary Examiner—Jerome D. Goldberg
(74) Attorney, Agent, or Firm—Fulbright & Jaworski L.L.P.

(57) ABSTRACT

Celecoxib, a COX-2 specific non-steroidal anti-inflammatory agent, is provided in combination with DFMO for the prevention and/or treatment of cancers. Provided with the present invention are pharmaceutically acceptable compositions that include a non-steroidal anti-inflammatory agent, celecoxib, together with an effective amount of difluoromethylornithine.

24 Claims, 3 Drawing Sheets

DFMO AND CELECOXIB IN COMBINATION FOR CANCER CHEMOPREVENTION AND THERAPY

This application claims priority to U.S. Provisional Application Serial No. 60/134,582, filed May 17, 1999.

BACKGROUND OF THE INVENTION

I. Field of the Invention

The present invention relates generally to the fields of cancer biology and biochemistry. More particularly, the present invention is directed to a method of cancer chemotherapy in mammals.

II. Description of Related Art

1. NSAIDS

There is an increasing body of experimental and epidemiological data suggesting that aspirin, and some other non-steroidal anti-inflammatory drugs (NSAID), exert a chemopreventive action on colorectal cancers and maybe also on stomach, esophagus (Thun et al., 1993) and even bladder (Earnest et al., 1992) cancers. Aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model and flurbiprofen has demonstrated anti-tumor effects in the APC(Min)+ mouse model (Wechter et al., 1997). NSAIDs also inhibit the development of tumors harboring an activated Ki-ras (Singh and Reddy, 1995).

NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, is a function of their ability to inhibit prostaglandin synthesis (reviewed in DuBois et al., 1996; Lupulescu, 1996; Vane and Botting, 1997). It is hypothesized that this may be effected by the inhibition of cyclooxygenase (COX) activity, which suppresses the synthesis of proinflammatory prostaglandins (Hinz et al., 1999). Epidemiological and laboratory studies suggest that colon carcinogenesis is, at least in part, mediated through modulation of prostaglandin production by COX isozymes (COX-1 and -2) (Kawamori, T., et al. 1998). Recent studies, however, indicate that NSAIDs may inhibit carcinogenesis through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a). It is hypothesized that a potential mechanism of sulindac activity may be the direct or indirect inhibition of tyrosine kinase (Winde et al., 1998), rather than the COX inhibition of the other NSAID agents.

Several NSAIDs have been examined for their effects in human clinical trials. A phase IIa trial (one month) of ibuprofen was completed and even at the dose of 300 mg/day, a significant decrease in prostoglandin $E_2$ ($PGE_2$) levels in flat mucosa was seen. A dose of 300 mg of ibuprofen is very low (therapeutic doses range from 1200–3000 mg/day or more), and toxicity is unlikely to be seen, even over the long-term. However, in animal chemoprevention models, ibuprofen is less effective than other NSAIDs. Studies have suggested a beneficial effect of the NSAID, aspirin, on colon cancer incidence, with effects being evident only at a weekly total dose of 1000 mg or greater (Giovannucci et al., 1996). However, three large cohort studies have produced conflicting reports on the beneficial effect of aspirin (Gann et al., 1993; Giovannucci et al., 1996; Greenberg et al., 1993). One group of investigators has recently shown that $PGE_{2\alpha}$ can be decreased at a dose between 80 and 160 mg/day. In contrast, another group of investigators have shown no such effect on colon mucosal prostaglandins at these low doses of aspirin, although substantial education of prostaglandins in upper gastrointestinal mucosa was demonstrated. The results of these studies indicate that a dose of aspirin of 80 mg is at the threshold of effect of this agent on colon mucosa. Thus, aspirin is not generally recommended for the primary chemoprevention of colorectal cancer in the general population due to questions regarding its efficacy coupled with significant risks of serious cerebrovascular and gastrointestinal adverse effects associated with long-term aspirin use (Singh, 1998).

The NSAID piroxicam is the most effective chemoprevention agent in animal models (Pollard and Luckert, 1989; Reddy et al., 1987; Ritland and Gendler, 1999), although it demonstrated side effects in a recent IIb trial. A large meta-analysis of the side effects of the NSAIDs also indicates that piroxicam has more side effects than other NSAIDs (Lanza et al., 1995). In addition, it has been suggested in at least one study that while tumors of the upper gastrointestinal tract are susceptible to pyroxicam treatment, those of the duodenum and colon are relatively resistant (Ritland and Gindler, 1999). Sulindac has been shown to produce regression of adenomas in Familial Adenomatous Polyposis (FAP) patients (Muscat et al, 1994), although at least one study in sporadic adenomas has shown no such effect (Ladenheim et al., 1995).

2. DFMO

α-Difluoromethylornithine (DFMO) is an enzyme-activated, irreversible inhibitor of ornithine decarboxylase (ODC) and causes depletion in the intracellular concentrations of putrescine and its derivative, spermidine (Pegg, 1988). Levels of spermine, which is derived from spermidine, are not as markedly affected by the enzyme inhibition. DFMO was initially synthesized for therapeutic anticancer usage, but it was found not to be an active cytotoxic agent in chemotherapy trials against human cancer (McCann and Pegg, 1992), except perhaps demonstrating moderate activity in the treatment of malignant brain tumors (Levin et al., 1987). In general, the compound was nontoxic, with the significant exception of hearing loss, which was reversible after the drug treatment was discontinued (Meyskens et al., 1986). The onset of the hearing loss could be associated with total cumulative dose (Croghan et al., 1991).

In experimental animal models, DFMO is a potent inhibitor of carcinogenesis that is especially active in preventing carcinogen-induced epithelial cancers of many organs, including those of the colon (Weeks et al., 1982; Thompson et al., 1985; Nowels et al., 1986; Nigro et al., 1987). DFMO acts late in the tumor-promotion phase in animals, but the precise mechanism by which it inhibits the development of polyps and cancers is unknown. Effects on cell transformation, invasion, and angiogenesis by ornithine decarboxylase and polyamines have been reported (Auvinen, 1997); for example, overexpression of ODC enhances cellular transformation and invasion (Kubota et al., 1997).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Singh et al., 1993; Reddy et al., 1990; Kulkarni et al., 1992). In one study, administration of DFMO or piroxicam to AOM-treated rats reduced the number of tumors harboring Ki-ras mutations from 90% to 36% and 25% respectively (Singh et al., 1994). Both agents also reduced the amount of biochemically active p21 ras in existing tumors. (Singh et al., 1993). Despite the success of the drugs in model systems, phase I trials conducted with this combination resulted in a range of adverse side effects (Carbone et al., 1998).

Studies have also been conducted in which DFMO was combined with aspirin to evaluate its chemopreventive effect in to AOM-treated rats. The combination of aspirin and DFMO administered after AOM was found to be synergistic (Li et al., 1999). The results demonstrated that the aspirin and DFMO combination could prevent colon cancer when administered after AOM (Li et al., 1999).

There remains a need for effective and less toxic methods for treating cancers. Current treatment protocols, especially those for colon cancers and polyps, include tumor resection, chemotherapy and radiation therapy. Colorectal cancer is the second leading cause of death from cancer in The United States.

SUMMARY OF THE INVENTION

Accordingly, it is the object of the present invention to provide a novel method for preventing and/or treating cancer in a patient comprising administering an effective amount of difluoromethylornithine (DFMO) in combination with celecoxib.

It is another object of the present invention to provide a novel method for preventing and/or treating cancer in a patient comprising administering a dose of DFMO of about 0.05 to about 5.0 gm/M$^2$/day, and preferably 0.05 to about 0.50 gm/M$^2$/day and a dose of celecoxib of about 10 to 1500 mg/day, and preferably 100 to 400 mg/day.

It is another object of the present invention to provide a novel method for preventing and/or treating cancer in a patient, wherein the cancer is colon cancer, breast cancer, pancreatic cancer, brain cancer, lung cancer, stomach cancer, a blood cancer, skin cancer, testicular cancer, prostate cancer, ovarian cancer, liver cancer, esophageal cancer, familial adenomatous polyposis.

It is another object of the present invention to provide a novel method for preventing and/or treating cancer in a patient comprising administering an effective amount of difluoromethylornithine (DFMO) in combination with celecoxib to said patient wherein DFMO is administered prior to celecoxib, wherein DFMO is administered after celecoxib, wherein DFMO is administered at the same time as celecoxib, wherein DFMO is administered at least a second time, or wherein celecoxib is administered at least a second time.

It is another object of the present invention to provide a novel method for preventing and/or treating cancer in a patient, following resection of a solid tumor, wherein DFMO and celecoxib are administered prior to said resection or are administered after said resection.

It is another object of the present invention to provide a novel method for preventing and/or treating cancer in a patient, wherein the DFMO and celecoxib are administered directly to said tumor, are administered systemically, are administered into the regional vasculature of said tumor, are administered into the region lymph system of said tumor, or are administered by different routes.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
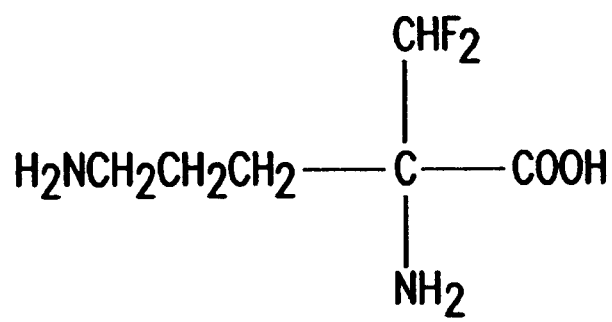
FIG. 1. Structural formula for DFMO.
Figure 2:
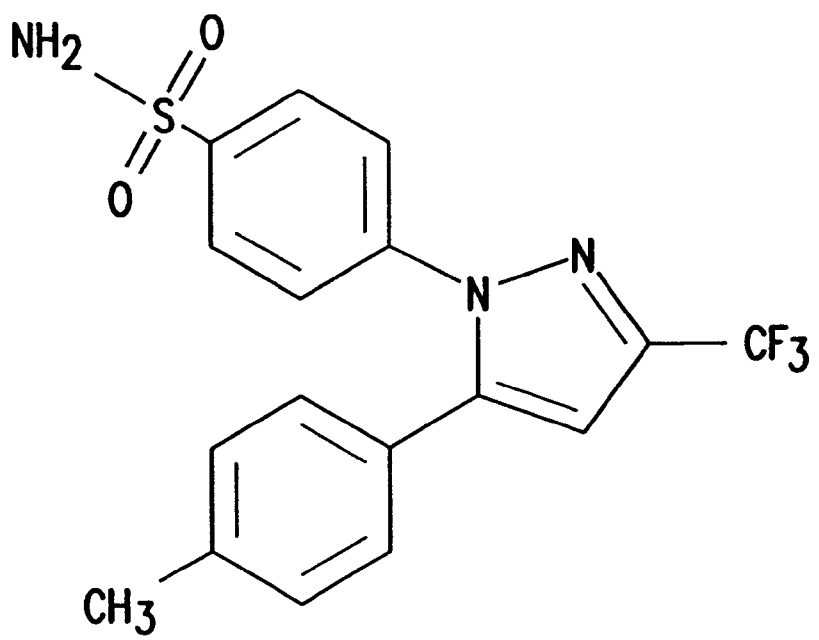
FIG. 2. Structural formula for celecoxib.

There is a need for effective and less toxic methods for preventing and/or treating cancers. Current treatment protocols include tumor resection, chemotherapy and radiation therapy. The present invention concerns the development of an effective and safe drug combination that will improve the prognosis of certain cancers. DFMO and celecoxib can be used to inhibit the growth of the cancer cells, kill the cancer cell outright, inducing apoptosis, inhibiting metastasis, reducing overall tumor burden, inducing tumor regression, or any combination of these. Their complementary action same pathway makes this combination more potent than either drug alone and better tolerated than either drug alone. This drug combination also serves to resolve a major problem in cancer, which is to prevent or effectively treat cancers without causing undue toxicity to patients. In this regard, chronic exposure at relatively low dosages is a preferred administration protocol.

A model for use of DFMO, alone or in combination with NSAIDS, has been the development of colon polyps and colon cancer. It is envisioned, in particular embodiments, that administration of this combination will result in an improved delay in the development of colon polyps in individuals susceptible to this condition. Also, it is envisioned that progression to full blown colon cancer and failure of colon cancer therapy can be substantially delayed by treatment regimens using DFMO and celecoxib. These advantages may be extended, in an analogous fashion, to other cancers.

I. Human Cancers

The present invention involves the delivery of DFMO and the NSAID celecoxib to individuals to prevent, inhibit or kill cancer cells. In one embodiment, the present invention also involves the delivery of therapeutic compounds to individuals exhibiting pre-cancerous symptoms to prevent the onset of cancer. Cells of this category include polyps and other precancerous lesions, premalignancies, preneoplastic or other aberrant phenotype indicating probable progression to a cancerous state.

In another embodiment, the present invention involves the delivery of therapeutic compounds to individuals exhibiting primary malignancies to limit, halt or reverse the tumor growth or to prevent metastasis. Target cancer cells include cancers of the lung, brain, prostate, kidney, liver, ovary, breast, skin, stomach, esophagus, head and neck, testicles, colon, cervix, lymphatic system and blood.

In yet another embodiment, the present invention involves the specific killing of tumor cells. Killing may be achieved by apoptotic or non-apoptotic mechanism. Again, a wide variety of tumor types are contemplated as within the scope of the disclosed therapies. The following are provided by way of example only.

1. Kirsten-Ras Dependent Cancers

Ras defines a protooncogene product that is found on chromosome 11. It is found in normal cells, where it helps to relay signals by acting as a switch (Lowy and Willumsen, 1993). When receptors on the cell surface are stimulated (by a hormone, for example), Ras is switched on and transduces signals that tell the cell to grow. If the cell-surface receptor is not stimulated, Ras is not activated and so the pathway that results in cell growth is not initiated. In about 30% of human cancers, Ras is mutated so that it is permanently switched on, telling the cell to grow regardless of whether receptors on the cell surface are activated or not. Point mutations in the cellular ras gene (c-ras) also can result in a mutant p21 protein that can transform mammalian cells.

Ras is a family of retrovirus-associated DNA sequences originally isolated from Harvey (H-ras, Ha-ras, rasH) and Kirsten (K-ras, Ki-ras, rasK) murine sarcoma viruses. Ras genes are widely conserved among animal species and sequences corresponding to both H-ras and K-ras genes have been detected in human, avian, murine, and non-vertebrate genomes. The closely related N-ras gene has been detected in human neuroblastoma and sarcoma cell lines. All genes of the family have a similar exon-intron structure and each encodes a p21 protein 2. Familial Adenomatous Polyposis, Syndrome, Gene Familial Adenomatous Polyposis (FAP), an inherited polyposis syndrome, is the result of germ-line mutation of the adenomatous polyposis coli (APC) tumor suppressor gene (Su et al., 1992). This autosomal-dominant condition with variable expression is associated with the development of hundreds of colonic adenomas, which uniformly progress to adenocarcinoma by forty years of age, two decades earlier than the mean age diagnosis for sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as the polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death.

II. Difluoromethylornithine (DFMO)

DFMO, also know as eflornithine, has the following chemical designation; 2-(difluoromethyl)-DL-ornithine. It is an inhibitor of ornithine decarboxylase, the rate limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

In recent years, chemotherapeutic agents that directly inhibit polyamine synthesis have been developed. Difluoromethylornithine (DFMO), one such drug, is an irreversible inhibitor of ODC and potentially can be given continuously with significant anti-tumor effects. This drug is relatively non-toxic at low doses of 0.4 $gr/M^2/day$ to humans while producing inhibition of putrescine synthesis in tumors. Studies in a rat-tumor model demonstrate that DFMO infusion can produce a 90% decrease in tumor putrescine levels without suppressing peripheral platelet counts.

Side effects observed with DFMO include effects on hearing at high doses of 4 $gr/M^2/day$ that resolve when it is discontinued. These effects on hearing are not observed at lower doses of 0.4 $gr/M^2/day$ when administered for up to one year (Meyskens et al., 1994). In addition a few cases of dizziness/vertigo are seen that resolve when the drug is stopped. Thrombocytopenia has been reported predominantly in studies using high "therapeutic" doses of DFMO (>1.0 $g/m^2/day$) and primarily in cancer patients who had previously undergone chemotherapy or patients with compromised bone marrow. Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. DFMO may inhibit proliferative repair processes, such as epithelial wound healing.

Although DFMO can effectively block tumor putrescine biosynthesis, the resultant antitumor effect is cytostasis and not cytotoxicity. For example, DFMO reduces the growth rate of an MCA sarcoma but does not produce tumor regression. This finding is consistent with reports of other investigators who showed that DFMO is a cytostatic agent. However, studies indicate that a significant role exists for DFMO agents, permitting the future development of combination chemotherapeutic regimens which incorporate DFMO.

DFMO and its use in the treatment of benign prostatic hypertrophy are described in two patents, U.S. Pat. Nos.

4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. U.S. Pat. No. 4,330,559 describes the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally, or parenterally.

The initial promise of DFMO as a therapeutic ODC inhibitor for use in the treatment of various neoplasias has dimmed somewhat because, although DFMO does, in fact, irreversibly inhibit ODC activity, cells treated in vivo with DFMO significantly increase their uptake of exogenous putrescine as described in U.S. Pat. No. 4,925,835. The intercellular transport mechanisms of the cell do an "end run" around the DFMO-impaired ODC activity by importing putrescine from the extra-cellular milieu. Therefore, DFMO's effect in vivo is far poorer than in vitro. So, while DFMO treatment effectively inhibits intracellular putrescine neogenesis, it also results in increased uptake of extracellular putrescine, thereby offsetting its ODC inhibitory effect.

This problem is compounded by the fact that putrescine is present in many common foods, such as orange juice, which contains approximately 400 ppm putrescine. This makes it virtually impossible to provide a patient a nutritionally sufficient diet which is free of putrescine. Therefore, DFMO-treated cells are capable of importing sufficient amounts of extracellular putrescine to support cell division.

Another drawback to DFMO is that, although it is a small molecule, it is relatively expensive to synthesize. The need for fluorination of a starting material or intermediate requires increased safety precautions and equipment which makes DFMO compounds difficult to synthesize at low cost.

However, because DFMO is an effective inhibitor of ODC, some researchers are attempting to use DFMO as part of a conjunctive treatment in combination with other therapeutic agents. For instance, U.S. Pat. No. 4,499,072, describe improving the polyamine-depletion effects of ODC inhibitors (including DFMO) by using interferon in combination with the ODC inhibitor. Additionally, it describes the use of both an ODC inhibitor and interferon in conjunction with a known cytotoxic agent such as methotrexate. U.S. Pat. No. 5,002,879, describe a similar conjunctive therapy in which an ODC inhibitor, preferably DFMO, is used in combination with lymphokine-activated killer (LAK) cells and interleukin-2.

Alternative strategies to make DFMO more acceptable to human patients are described in U.S. Pat. No. 4,859,452 (incorporated by reference). Formulations of DFMO are described which include essential amino acids in combination with either arginine or ornithine to help reduce DFMO-induced toxicities.

III. NSAIDs and Celecoxib

NSAIDs are anti-inflammatory agents that are not steroids. In addition to antiinflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. (AMA Drug Evaluations Annual, 1994, p 1814–5). Sulindac, piroxicam, aspirin and indomethacin all are examples of NSAIDS.

NSAIDs induce apoptosis in both colon tumor cell lines and animal tissues, and appear to inhibit Ki-ras activation in tumors; however, the activation of Ki-ras has not yet been investigated as a mechanism of NSAID-mediated cytotoxicity. It also is not known if such cytotoxicity is dependent on the anti-inflammatory properties of the NSAIDs. The NSAID sulindac, which also inhibits Ki-ras activation, is metabolized to two different molecules which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis.

The present invention is concerned, primarily, with the new NSAID, celecoxib. Sold by Searle under the trade name CELBREX™, celecoxib is chemically designated as 4-[5-(4-methyphenyl)-3-(trifluoromethyl)-1H-pyrazol-1-yl] benzenesulfonamide. The empirical formula is $C_{17}H_{14}F_3N_3O_2S$, and the molecular weight is 381.38. CELEBREX™ is marketed in 100 or 200 mg oral capsules.

Celecoxib exhibits anti-inflammatory, analgesic and anti-pyreti activities in animal models. The mechanism of action is thought to be the result of inhibition of prostaglandin synthesis. The enzyme cyclooxygenase-2, or "COX-2," is an important enzyme in this pathway. Selective inhibition of COX-2 (the related enzyme COX-1 is not inhibited) is a unique characteristic of celecoxib, and is believed to reduce potential gastrointestinal toxicities associated with inhibition of COX-1.

1. Pharmacokinetics

Peak plasma levels of celecoxib are roughly 3 hours after an oral dose. When take with a high fat meal, plasma levels were delayed about 1–2 hours, with an increase in total absorption of 10–20%. Aluminum or magnesium containing antacids resulting in a decrease in plasma concentrations. Celecoxib is highly protein bound with the clinical dose range, with in vitro studies indicating that albumin and alpha$_1$-acid glycoprotein being the major bound species. Cytochrome P450 2C9 is the major metabolizing enzyme of celecoxib. The three primary metabolites are the alcohol, the corresponding carboxylic acid and its glucuronide conjugate; these metabolites are inactive as COX-1 and COX-2 inhibitors. Following a single dose, 57% of the dose was excreted in feces, and 27% in the urine. The effective half-life is roughly 11 hours under fasted conditions.

2. Patient Populations

Geriatric patients had high maximal serum concentrations, and elderly male had high concentrations than elderly females. For elderly patients of less than 50 kg, lower doses should be used initially. Blacks show higher serum concentrations than Caucasians. Hepatic insufficiency increases serum concentration, while renal insufficiency decreases concentration.

3. Drug Interactions

Patients should be questioned regarding the use of drugs that inhibit cytochrome P450 2C9. Specific potential drug interactions include fluconazole and lithium, and possibly furosemide and ACE inhibitors.

4. Side Effects and Contraindications

Side effects for NSAIDs typically include gastroduodenal and gastrointestinal irritation. However, celecoxib shows far less of these effects than other NSAIDs. Other possible side effects include anaphylactoid reactions, although none have been reported for celecoxib. It also should be avoided for patients with advanced renal disease and pregnant mothers.

5. Combinations of NSAIDs

Combinations of various NSAIDs also may be used for according to the present invention. For example, by using lower doses of celecoxib and one or more other NSAIDs (e.g., aspirin, piroxicam, sulindac), it is possible to reduce the side effects or toxicities associated with higher doses of individual NSAIDs. Specifically for the purposes outlined in this invention, celecoxib can be used in combination with other NSAIDs in this manner.

IV. Min Mouse Model

The Min (multiple intestinal neoplasia) mouse, as a model of familial adenomatous polyposis (FAP), has provided important insights into the phenotype of the mutated APC/Apc gene (Lipkin, 1997). The Min mouse can develop greater than 100 gastrointestinal adenomas/adenocarcinomas throughout the gastrointestinal tract by 120 days of life leading to GI bleeding, obstruction and death. The present invention will utilize this model in combined DFMO/celecoxib treatments of gastrointestinal tumors.

1. The Model

Mice, purchased from The Jackson Laboratory (Bar Harbor, Maine), were bred crossing C57BL/6J-Apc$^{Min/+}$ males and C57/BL6 females. Heterozygous Min mice (Apc$^{Min}$/Apc$^+$): (heterozygous for a nonsense mutation at codon 850 of Apc) were identified by genotyping at weaning by an allele specific PCR™ assay using tail-tip DNA. Homozygous (Apc$^+$/Apc$^+$) litter mates served as controls. Treatments may comprise supplementing drinking water with DFMO and or celecoxib (Merrell Dow Research Inst.). In other treatments, celecoxib or DFMO can be added to AIN-93G mouse diet.

2. Tissue Collection

Mice are sacrificed through $CO_2$ asphyxiation. The small intestine and colon segments are removed from mice and dissected lengthwise, mounted and fixed in 70% ethanol, and placed at 4° C. for tumor scoring. Representative tissues are taken for histopathology evaluation.

3. Proliferating Cell Nuclear Antigen

Ethanol fixed, paraffin-embedded sections of mouse small intestine and colon are evaluated by immunohistochemistry using a monoclonal anti-PCNA PC 10 antibody (Oncogene Science). Standardized scoring methods are used to calculate a proliferative index based on an average of 15–20 villus-crypts (intestine) or crypt columns (colon) per sample.

4. Apoptosis Staining

Alterations in nuclear morphology (condensed chromatin, distinct apoptotic bodies) are the main endpoint for scoring tissue in well-oriented crypts and villi using standardized protocols to calculate the percent apoptotic cells per total counted.

5. Polyamine Assay

Polyamine (putresoine, spermidine, and spermine) levels are determined in acid-extracted samples by reverse-phase high performance liquid chromatography. The residual acid insoluble pellet is assayed for protein content by BCA (Pierce) with data expressed as nanomoles polyamine per mg protein.

6. Ornithine Decarboxylase (Odc) and Spermidine/spermnen$^1$-acetyltransferase (N$^1$ssat) Gene Expression Total RNA from whole intestine and colon is isolated using TRIzol reagent (Gibco, BRL). Northern blots are prepared and then hybridized with a $^{32}$P-labeled cDNA encoding for mouse ODC and for human N$^1$SSAT utilizing a random priming technique (Boehringer Mannheim). Data is expressed (relative gene expression) as the ratio of the integrated $^{32}$P-labeled hybridization band for the gene of interest and the integrated density of ethidium bromide stained 18S ribosome band.

Alterations in ODC gene expression and polyamine content are present in small intestinal and colonic tissues of Min mice when compared to litter mate controls. These findings are consistent with the disturbances of polyamine physiology that have been previously described in FAP patients (Luk et al., 1984; Giardiello et al., 1997). In the Min mouse model, tissue polyamine contents are elevated in the small intestines, but not the colon. The increased polyamine content. in the small intestines was associated with an increase in ODC, and a decrease in antizyme, steady state RNA levels. These two changes would predict increased ODC-dependent polyamine contents in the small intestines of these mice.

7. Measuring Drug Effects

There are a number of parameters that can be assessed to determine the efficacy of a particular treatment. These include, but are not limited to: (a) animal survival, (b) food intake, (c) weight loss/gain, (d) number of lesions, (e) size of lesions, (f) occurrence of metastasis, (g) activity.

V. Routes of Administration and Formulation

According to the present invention, one may treat a patient by direct injection of a tumor or its vasculature with the therapeutic compounds. Alternatively, the tumor may be infused or perfused with the therapeutic compounds using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

An exemplary course of treatment, for a primary tumor or a post-excision tumor bed, could involve multiple doses. During a course of treatment, the need to complete the planned dosings may be re-evaluated. Various combinations of DFMO and celecoxib may be employed, either used sequentially or simultaneously. For instance, where DFMO is "A" and the celecoxib is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

The time between treatment of celecoxib and DFMO may be for a period from about 1–2 hours, to about 2–6 hours, to about 6–12 hours, to about 12–24 hours, to about 1–2 days, to about 1–2 wk or longer following the initiation of treatment. Alternatively, simultaneous administration of DFMO and celecoxib, with or without sequential administration of either DFMO or celecoxib could also be employed. For instance where DFMO is "A" and the celecoxib is "B" and "AB " is both together:

AB/A A/AB B/AB AB/B AB/AB AB/AB/AB
AB/A/A AB/B/B AB/A/B AB/B/A A/AB/B A/AB/A
B/AB/B B/AB/A A/B/AB A/A/AB B/B/AB B/A/AB
AB/AB/A AB/AB/B AB/A/AB AB/B/AB A/AB/AB
B/AB/AB

Results of the therapeutic treatments described above using the combination of DFMO and celecoxib on patients with tumors can vary. The therapy may inhibit the growth of the cancer cells, kill the cancer cell outright, induce apoptosis, inhibit metastasis, reduce overall tumor burden, induce tumor regression, or any combination of these. Any and all of these results are advantageous to the patient.

Aqueous compositions of the present invention comprise an effective amount of the therapeutic compound, further dispersed in pharmaceutically acceptable carrier or aqueous medium. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Where clinical application of liposomes containing therapeutic compounds is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance.

Formulations for DFMO are disclosed in WO 98/25603 and WO/98/19667, both of which are incorporated by reference.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Human Treatment Protocol for the Combination of DFMO and Celecoxib

The dose of the drugs is (a) celecoxib 150 mg, orally, each day (b) and DFMO 0.25/gm/day. The course of treatment will be determined by the efficacy and toxicity, but may be as short as I month, and potentially indefinitely.

Baseline urine and blood tests will be performed and include, chemistry panel, CBC (includes liver function tests, amylase, lipase, BUN, creatinine, and complete blood counts). Six particular areas of consideration, with regard to side effects, are:

Thrombocytopenia (Low Platelet)

Thrombocytopenia has been reported predominantly in studies using "therapeutic" doses of DFMO ($>$g/m$^2$/day) and primarily in cancer patients who had previously undergone chemotherapy or patients with compromised bone marrow.

Wound Healing

DFMO may inhibit proliferative repair processes, such as epithelial wound healing. In DFMO studies employing administrations up to one year in duration—some of which included similar rectal biopsy procedures—those theoretical problems with wound healing have not been experienced. In the current protocol, which provides for extended dosing over a three-year period, this potential toxicity is monitored with vigilance. Second, the rectal biopsy procedure (sigmoidoscopy) performed during the study carries a very low risk of perforation of the rectum and of post-biopsy bleeding. No problems have been seen in the patients on the phase IIa trial nor have there been seen this side effect in ongoing phase I studies being conducted by other investigators. However, in those patients undergoing an occasional biopsy of the polyp greater than 1 cm the drugs are held for one week. Systemic infection from this breach of rectal mucosal integrity is also a remote possibility. Third, a colonoscopy is required for inclusion in and at completion of the study. This also carries the same risks as sigmoidoscopy plus an added risk of hemorrhage if polyps are found and removed by biopsy or electrocautery excision. It should be noted that the colonoscopies will be scheduled consistent with standard care for patients with prior polyps and do not represent an "extra" procedure.

Ulceration

NSAIDs can cause gastrointestinal ulceration that in general is dose-related. Its potential interaction with DFMO effect (i.e., possible delay in wound healing) is unknown. A significant portion of this problem may be due to the presence of *H. pylori* and therefore only patients that are antibody negative or who have undergone a course of antibiotics will be eligible for trial. Subjects are carefully monitored and have a CBC drawn every 6 months to detect occult blood loss.

Hearing Loss

Hearing loss may occur in association with DFMO administration at high doses. In a previous study (Croghan et al., 1991), it was reported that less than 10% of the patients who received cumulative doses below 150 g/m$^2$ developed a demonstrable hearing deficit, while hearing losses were observed in up to 75% of patients who received cumulative doses above 250 g/m$^2$. This side effect has been totally reversible upon drug discontinuation. In two phase I trials done by other investigators, no audiometric changes were seen after about 6 months of DFMO at 0.50 g/m$^2$/d (total dose 90 gm) although changes were seen at higher doses. Additionally, with DFMO at the highest dose group (0.4 gm/m$^2$/day), which represents a total dose of 144 mg/m$^2$ no detectable audiologic change was observed. At low doses of DFMO, ongoing recovery of inner ear polyamines may occur and hearing loss will be rare. The dose chosen for the trial is 0.25 g/m$^2$/d. If hearing loss is detected, it should not occur until after 800 days.

Venous Access

Blood specimens are obtained from an arm vein, carrying the risk of bruising and local infection.

*H. pylon*

A considerable amount of data indicates that *H. pylori* positivity may contribute significantly to NSAID toxicity. The risk of developing peptic ulcer disease increases with use of long-term, high dose NSAIDs to 3- to 4-times that of non-users. A preexisting *H. pylori* infection increases the risk of gastric ulcer 3- to 4-fold. To reduce possible risk to patients, a serum antibody screen will be obtained. Those who are positive will undergo a 2 week prophylactic course of "triple therapy" before randomization.

A preferred regimen at this time includes omeprazole 20 mg by mouth twice a day, metronidazole 250 mg or 500 mg by mouth four times a day, and clarithrymycin 250 mg or 500 mg by mouth three times a day (regimen referred to as MOC). At this time a fourteen day course is recommended, however, studies have shown that a seven day course is as effective in eradicating the infection. Adverse effects possible from this triple therapy are dizziness (2%) with omeprazole; metallic taste, vomiting, anorexia, headache, fever, rash (5%), neuropathy, and disulfiram-like reaction with alcohol ingestion (20%) with metronidazole. Clarithrymycin may cause diarrhea (10%) nausea, dyspepsia, headache, and rarely, pseudomembranous colitis (1%). All participants who are on this regimen prior to enrollment are monitored closely for any adverse reactions.

Another favored triple treatment regimen includes twice daily doses of lansoprazole, 30 mg, amoxicillin 1 gm, and clarithrymycin 500 mg. This easy to follow dosing regimen is recommended to be 10 to 14 days in length for optimal treatment of *H. pylori*. Possible adverse effects are: with lansoprazole—headache (5%), diarrhea (8%), nausea (3%); with amoxicillin—diarrhea and super-infections; and with clarithrymycin—diarrhea (10%), nausea, dyspepsia, headache, and rarely, pseudomembranous colitis (1%). Participants are solicited for comments regarding possible side effects while on this prophylactic regimen.

EXAMPLE 2

Delayed Regrowth of HT-29 Colon Tumors in Mice with a Combination of DFMO and Celecoxib The regrowth of colon tumors in mice is observed to determine the activity of the DFMO when used alone and in combination with celecoxib. The human colon adenocarcinoma tumor line, HT-29, is downstaged with CPT-11 (irinotecan, or Camptosar®, a trademark of Pharmacia & Upjohn.). Mice are evaluated for up to 100 days, and sacrificed when a tumor size of 1000 mg is reached. The weight of the tumor is calculated using caliper measurements of width (W) and length (L) in millimeter units with the formula:

$$\text{Weight (mg)}=W^2 \times L/2.$$

The in vivo evaluation is done using female nu/nu BALBc mice with an initial weight of about 20 g. Mice were placed in four experimental and one control groups of ten mice each and were evaluated for tumor regrowth as measured by tumor weight and survival rate. Subcutaneous implants are done using a trocar fragment of about 5×5 mm. The mice were given CPT-11 on Day 1 of the experiment at a dose of 100 mg/kg.

One group of mice was given CPT-11 ip qw×3. Another group consists of animals given the same initial dose of CPT-11 and a solution of 3% DFMO given in the drinking water daily. A third group consists of animals given the initial dose of CPT-11 and 3 mg/kg celecoxib given by mouth, twice daily. The last group consists of animals given the initial dose of CPT-11, a solution of 3% DFMO in drinking water given daily, and 3 mg/kg celecoxib given by mouth, twice daily.

Figure 3:
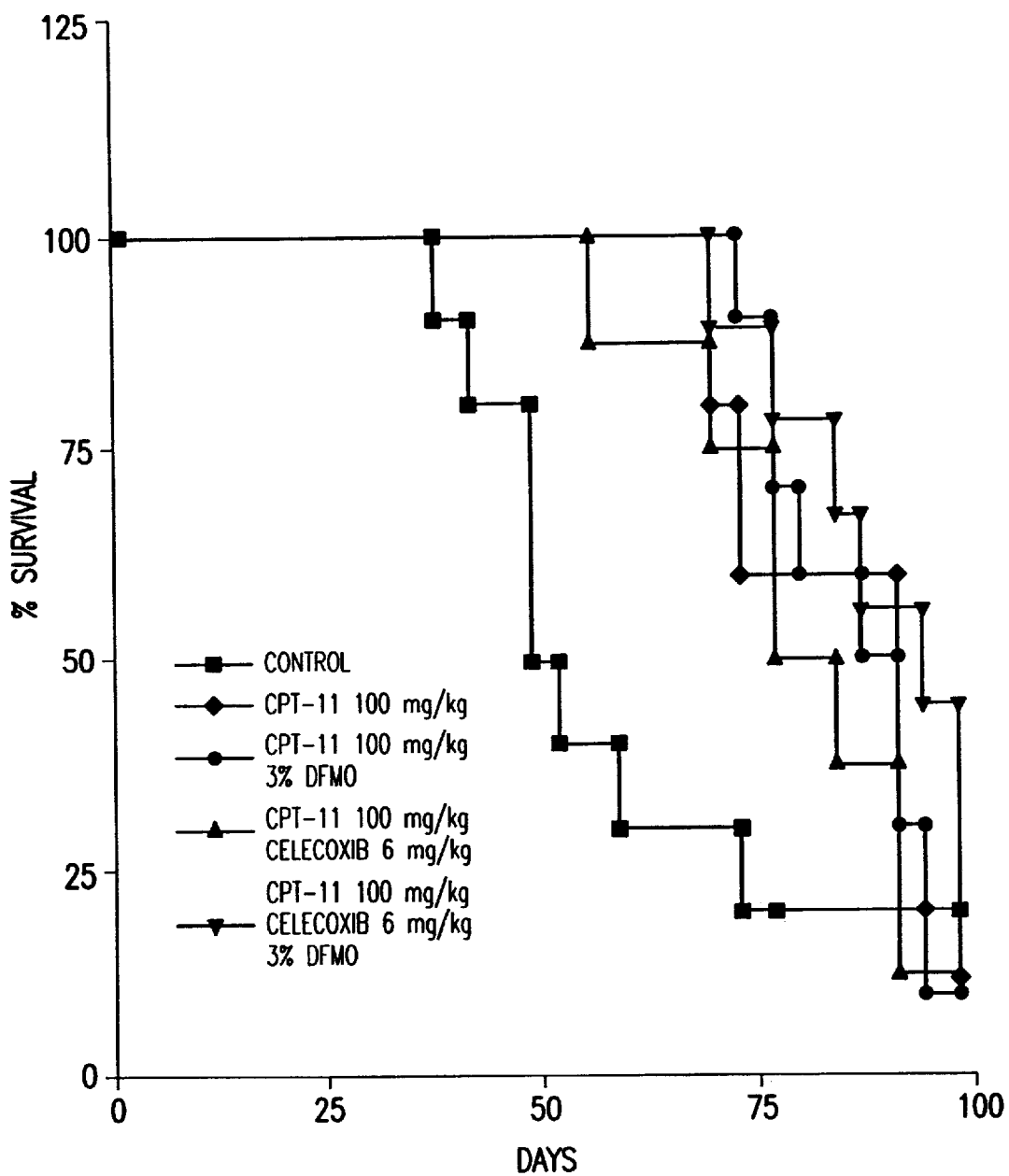
FIG. 3. Percent survival for the HT-29 human colon tumor line for mice downstaged with CPT-11. The mice were treated with DFMO, celecoxib, or a combination of DFMO and celecoxib. All mice are female nu/nu BALBc weighing about 20 g. The mice have been treated with: no CPT-11, DFMO, or celecoxib (square); 100 mg/kg CPT-11 (diamond); 100 mg/kg CPT-11 and 3% DFMO (circle), 100 mg/kg CPT-11 and 6 mg/kg celecoxib (up triangle); and 100 mg/kg CPT-11, 6 mg/kg celecoxib, and 3% DFMO (down triangle).
Figure 4:
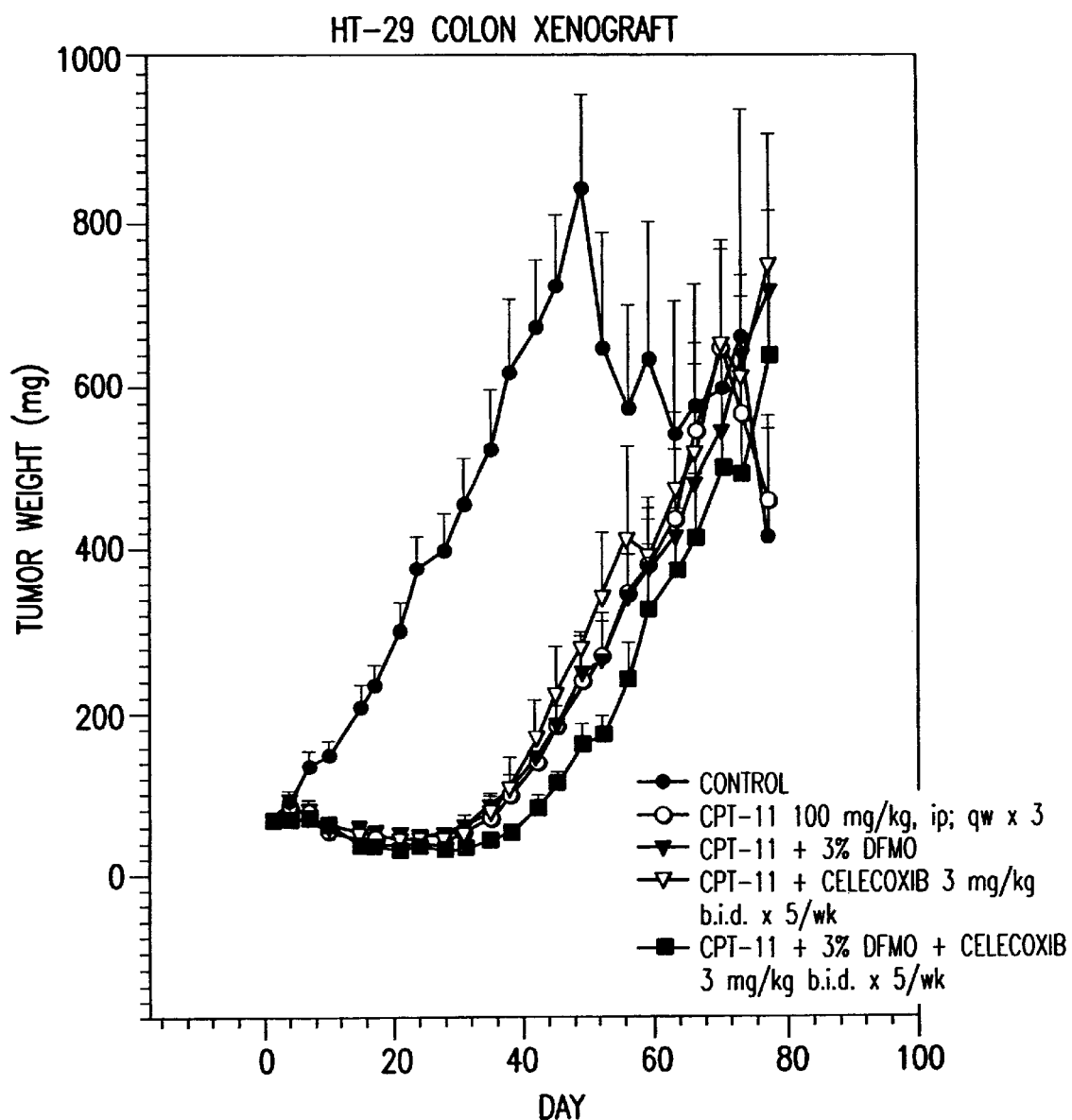
FIG. 4: The weight of tumor in mice from the HT-29 human colon tumor line is shown for mice treated with DFMO, celecoxib, or a combination of DFMO and celecoxib over the course of about 75 days. All mice are female nu/nu BALBc weighing about 20 g. Mice are pair matched at about 70 mg tumor weight. The mice have been treated with: no CPT-11, DFMO, or celecoxib (solid circle); 100 mg/kg CPT-11 (open circle); 100 mg/kg CPT-11 and 3% DFMO (solid triangle), 100 mg/kg CPT-11 and 3 mg/kg celecoxib given twice daily, five times a week (open triangle); and 100 mg/kg CPT-11, 3 mg/kg celecoxib given twice daily, five times week, and 3% DFMO (square). Error bars are one standard deviation.

Data showing the survival rate of the different experimental groups of mice are shown in FIG. 3. The survival rate of mice given both DFMO and celecoxib tends to be greater than that of the other groups. Similarly, FIG. 4 demonstrates that the tumor weight for mice given both DFMO and celecoxib remains the same or smaller than the tumor weight of the mice given either a single inhibitor or no drug treatment over a period spanning more than 75 days.

REFERENCES

The following references, to the extent that they provide exemplary procedural or other details supplementary to those set forth herein, are specifically incorporated herein by reference.

U.S. Pat. No. 4,413,141
U.S. Pat. No. 4,330,559
U.S. Pat. No. 4,925,835
U.S. Pat. No. 4,499,072
U.S. Pat. No. 5,002,879
U.S. Pat. No. 4,859,452
U.S. Pat. No. 5,814,625
U.S. Pat. No. 5,843,929
U.S. Pat. No. 4,496,588
U.S. Pat. No. 4,309,442

Alberts, Hixson, Ahnen, Bogert, Einspahr, Paranak, Brendel, Gross, Pamukcu, Burt, "Do NSAIDs exert their colon cancer chemoprevention activities through the inhibition of mucosal prostaglandin synthetase?" *J. Cell. Biochem. Supp.*, (22):18–23, 1995.

Arber, Han, Sgambato, Piazza, Delohery, Begemann, Weghorst, Kim, Pamukcu, Ahnen, Reed, Weinstein, Holt, "A K-ras oncogene increases resistance to sulindac-induced apoptosis in rat enterocytes," *Gastroenterology*, (113):1892–1990, 1997.

Ausubel, ed., "Current protocols in molecular biology," *New York: John Wiley & Sons*, 1995.

Auvinen, "Cell transformation, invasion, and angiogenesis: a regulatory role for ornithine decarboxylase and polyamines?," *J. Nat'l Cancer Inst.*,(89):533–7, 1997.

Bacus and Bacus, "A method of correcting DNA ploidy measurement in tissue sections," *Mod. Pathol.*, 7:652–666, 1994.

Bacus and Grace, "Optical microscope system for standardized cell measurement and analyses," *Appl. Optics.*, 26:3280–3293, 1987.

Bedi, Pasricha, Akhtar, Barber, Bedi, Giardiello, Zehnbauer, Hamilton, Jones, "Inhibition of apoptosis during development of colorectal cancer," *Cancer Res.* (55):1811–1816, 1995.

Braverman, Standiewicz, Goldstein, Patz, Morali, Jacobsohn," Ornithine decarboxylase: an unreliable marker for the identification of population groups at risk for colonic neoplasia," *Am. J. Gastroenterology*, 85:723–726, 1990.

Boolbol, Dannenberg, Chadburn, Martucci, Guo, Ramonetti., Abreu-Goris, Newmark, Lipkin, deCosse, Bertagnolli, "Cyclooxygenase 2 overexpression and tumor formation are blocked by sulindac in a murine model of familial adenomatous polyposis," *Cancer Res.*, (56):2256–2560, 1996.

Boyle, Meyskens, Garweal, Gerner, "Polyamine contents in rectal and buccal mucosae in human treated with oral difluoromethylornithine," *Cancer Epi Biomarkers Prev.*, 1:131–135, 1992.

Bumer, Loeb, "Mutations in the KRAS2 oncogene during progressive stages of human colon carcinoma," *Proc. Nat'l Acad. Sci. U.S.A.*, 86(7):2403–7, 1989.

Bussey, "Historical developments in familial adenomatous polyposis," In: Lemuel Herrera (ed), Familial Adenomatous Polyposis, pp. 1–22, Alan R. Liss, Inc. New York, 1990.

Carbone, Douglas, Larson, Verma, Blair, Pomplun, Tutsch, "Phase I chemoprevention study of piroxicam and alpha-difluoromethylornithine." *Cancer Epidemiol Biomarkers Prev* 7(10): 907–12, 1998.

Carethers, "The cellular and molecular pathogenesis of colorectal cancer," *Gastroenterology Clinics of North America*, (25):737–754, 1996.

Croghan, Aicken, Meyskens, "Dose-related α-difluoromethylornithine ototoxicity," *Am. J. Clin. Oncol.*, (14):331–5, 1991.

Delage, Chastre, Empereur, Wicek, Veissiere, Capeau, Gespach, Cherqui, "Increased protein kinase C alpha expression in human colonic Caco-2 cells after insertion of Ha-ras or polyoma virus middle T oncogenes," *Cancer Res.*, (53):2762–70, 1993.

DiSario, Alberts, Tietz, Khullar, Bohrman, Larsen, Hixson, Samowitz, Reading, Buys, Dawson, Burt, "Sulindac induces regression and prevents progression of sporadic colorectal adenomas," *Gastroenterology (AGA Abstract)*, April 1997.

DuBois, Giardiello, Smalley, "Nonsteroidal anti-inflammatory drugs, eicosanoids, and colorectal cancer prevention," *Gastroenterology*, (25):773–791, 1996.

Erdman, Wu, Hixson, Ahnen, Gerner, "Assessment of Mutations in Ki-ras and P53 in colon cancers from azoxymethane-and dimethylhydrazine-treated rats," *Mol. Carcin.*, (19):137–144, 1997.

Gann, Manson, Glynn, Buring, Hennedens, "Low-dose aspirin and incidence of colorectal tumors in a randomized trial," *J. Nat'l Cancer Inst.*, 85:1220–1224, 1993.

Gerner, Garewal, Emerson, Sampliner, "Gastrointestinal tissue polyamine contents of patients with Barrett's esophagus treated with a-difluoromethylornithine," *Cancer Epidemoil. Biomarkers Prev.*, 3:325–330, 1994.

Giardiello, Hamilton, Hylind, Yang, Tamez, Casero, "Ornithine decarboxylase and polyamines in familial adenomatous polyposis," *Cancer Res.*, (57):199–201, 1997.

Giovannucci, Rimm, Stampfer, Colditz, Ascherio, Willett, "Aspirin use and the risk for colorectal cancer and adenomas in male health professionals," *Ann. Intern. Med.*, 121:241–246, 1994.

Greenberg, Baron, Freeman, Mandel, Haile, "Reduced risk of large-bowel adenomas among aspirin users," *J. Nat'l Cancer Inst.*, 85:912–916, 1993.

Hanif, Pittas, Feng, Koutsos, Qiao, Staino-Coico, Shiff, Rigas, "Effects of nonsteroidal anti-inflammatory drugs on proliferation and on induction of apoptosis in colon cancer cells by a prostaglandin-independent pathway," *Biochemical Pharmacology*, (52):237–245, 1996.

Hinz, B. and K. Brune, "[In Process Citation]." *Wien Klin Wochenschr* 111 (3): 103–12, 1999.

Hixson, Emerson, Shassetz, Gerner, "Sources of variability in measurements of ornithine decarboxylase activity and polyamine contents in colorectal mucosa," *Cancer Epidemoil. Biomarkers Prev.*, 3:317–323, 1994.

Hixson, Garewal, McGee, Sloan, Fennerty, Sampliner, Gerner, "Ornithine decarbolylase and polyamines in colorectal nelplasia and adjacent nucosa," *Cancer Epidemiology Biomarkers Prev.*, 2:369–374, 1993.

Jiang, Kahn, Guillem, Lu, Weinstein, "Rapid detection of ras oncogenes in human tumors, applications to colon, esophageal, and gastric cancer," *Oncogene*, 4:923–928, 1989.

Kawamori, Rao, Seibert, Reddy, "Chemopreventive activity of celecoxib, a specific cyclooxygenase-2 inhibitor, against colon carcinogenesis." *Cancer Res* 58(3): 409–12, 1998.

Kerr, Winterford, Harmon, "Apoptosis: its significance in cancer and cancer therapy," *Cancer*, (73):2013–2026, 1994.

Kerr, Searle, Harmon, Bishop, "Apoptosis," In: *Perspectives on mammalian cell death*, Potten (ed), Oxford Press, NY, N.Y., 93–128, 1987.

Kerr, Wyllie, Currie, "Apoptosis: a basic biological phenomenon with wide-ranging implications in tissue kinetics," *Br. J. Cancer*, 26:239–257, 1972.

Keshgegian, Cnaan, "Proliferation markers in breast carcinoma. Mitotic figure counting, S-phase fraction, PCNA, Ki-67 and MIB-1," *Am. J. Clin. Pathol.*, 104:1042–1049, 1995.

Kingsnorth, King, Diekema, McCann, Ross, Malt, "Inhibition of ornithine decarboxylase with 2-difluoromethylornithine: reduced incidence of dimethylhydrazine-induced colon tumors in mice," *Cancer Res.*, (43):2545–2549, 1983.

Kubota, Kiyosawa, Nomura, Yamada, Seyama, "Ornithine decarboxylase overexpression in mouse 10T1/2 fibroblasts: cellular transformation and invasion," *J. Nat'l Cancer Inst.*,(89):567–71, 1997.

Kulkarni, Zang, Kelloff, Reddy, "Effect of the chemopreventive agents piroxicam and D,L-α-difluoromethylornithine on intermediate biomarkers of colon carcinogenesis," *Carcinogenesis*, (13):995–1000, 1992.

Ladenheim, Garcia, Titzer, Herzenbert, Lavori, Edson, Omary, "Effect of Sulindac on sporadic colonic polyps," *Gastroenterology*, 108:1083–1087, 1995.

Laemmli, "Cleavage of structural proteins during the assembly of the head of bacteriophageT4," *Nature*, 227(259): 680–5, 1970.

Lanza, Walker, Bortnichak, Dreyer, "Peptic ulcer and gastrointestinal hemorrhage associated with nonsteroidal anti-inflammatory drug use in patients younger than 65 years. A large health maintenance organization cohort study." *Arch. Intern. Med.*, 155:1371–1377, 1995.

Levin, Chamberlain, Prados, Choucair, Berger, Silver, et al., "Phase I-II study of eflornithine and mitogauzone combined in the treatment of recurrent primary brain tumors," *Cancer Treat. Rep.*, (71):459–64, 1987.

Li, Schut, Conran, Kramer, Lubet, Steele, Hawk, Kelloff, Pereira, "Prevention by aspirin and its combination with alpha-difluoromethylornithine of azoxymethane-induced tumors, aberrant crypt foci and prostaglandin E2 levels in rat colon." *Carcinogenesis* 20(3): 425–30, 1999.

Liao, Brewer, Zavada, Pastorek, Pasterekova, Manetta, Berman, DiSaia, Stanbridge, "Identification of the MN antigen as a diagnostic biomarker of cervical intraepithelial squamous and glandular neoplasi and cervical carcinomas," *Am. J. Pathol.*, 145:598–609, 1994.

Lipkin, "New rodent models for studies of chemopreventive agents," *J Cell Biochem Suppl* (28–29):144–7, 1997.

Losi, Roncucci, di Gregorio, de Leon, Benhattar, "K-ras and p53 mutations in human colorectal aberrant crypt foci," *Journal of Pathology*, 178(3):259–63, 1996

Lowy, Willumsen, "Function and regulation of ras," *Annu Rev Biochem* (62):851–91, 1993.

Luk, Baylin, "Onithine decarboxylase as a biological marker in familial colonic polyposis," *N. Eng. J. Med.*, (311): 80–83, 1984.

Lupulescu, "Prostaglandins, their inhibitors and cancer," *Prostaglandins, Leukotrienes, and Essential Fatty Acids*, (54):83–94, 1996.

Matter A: Microcinematographic and electron microscopic analysis of target cell lysis induced by cytotoxic T lumphocytes," *Immunology*, 36:179–190, 1979.

McCann, Pegg, "Ornithine decarboxylase as an enzyme target for therapy," *Pharmacol. Ther.*, (54):195–215, 1992.

Meyskens, Kingsley, Glatrke, Loescher, Booth, "A phase II study of α-difluoromethylornithine (DFMO) for the treatment of metastatic melanoma," *Invest. New Drugs*, (4):257–62, 1986.

Meyskens, Emerson, Pelot, Meshkinpour et al., "Dose de-escalation chemoprevention trial of α-difluoromethylornithine in patients with colon polyps," *J. Nat'l Cancer Inst.*, 86(15):1122–1130, 1994.

Meyskens, Gerner, "Development of difluoromethylornithine as a chemoprevention agent for the management of colon cancer," *J Cell. Biochem.*, 22:126–131, 1995.

Meyskens, Pelot, Meshkinpour, Plezia, Gerner, Emerson, "Preliminary results of a phase Iia of difluoromethylornithine (DFMO) to prevent colon cancer," In: *Cancer Chemoprevention*, Kelloff (ed), CRC Press, Inc., Boca Raton, Fla., 36:541–555, 1992.

Moorghen, Inc, Finney, Sunter, Appleton, Watson, "A protective effect of Sulindac against chemically-induced primary colonic tumors in mice," *J Pathol.*, 156:341–347, 1988.

Muscat, Stellman, Wynder, "Nonsteroidal antiinflammatory drugs and colorectal cancer," *Cancer*, 74:1847–1854, 1994.

Narisawa, Sato, Tani, Kudo, Takahashi, Goto, "Inhibition of development of methylnitrosourea-induced rat colon tumors by indomethacin treatment," *Cancer Research* 41(5):1954–7, 1981.

Nigro, Bull, Boyd, "Importance of the duration of inhibition on intestinal carcinogenesis by difluoromethylornithine in rats," *Cancer Lett.*, (35):183–8, 1987.

Nowels, Homma, Seidenfeld, Oyasu, "Prevention of the inhibitory effects of alpha-diflouromethylornithine on rat urinary bladder carcinogenesis by exogenous putrescine", *Cancer. Biochem. Biophys.*,(8):257–63, 1986.

Pasricha, Bedi, O'Connor, Rashid, Akhtar, Zahurak, Piantadose, Hamilton, Giardiello, "The effects of sulindac on colorectal proliferation and apoptosis in familial adenomatous polyposis," *Gastroenterology*, 109:994–998, 1995.

Payne, Bjore, Schultz, "Change in the frequency of apoptosis after low- and high-dose x-iradiation of human lymphocytes," *J. Leuk. Biol.*, 52:433–440, 1992.

Payne, Bernstein, Bernstein, "Apoptosis overview emphasizing the role of oxidative stress. DNA damage and signal transduction pathways," *Leukemia Lumphoma*, 19:43–93, 1995.

Pegg, "Recent advances in the biochemistry of polyamines in eukaryotes," *Biochem. J.*, (234):249–262, 1986.

Pegg, "Polyamine metabolism and its importance in neoplastic growth and a target for chemotherapy," *Cancer Res.*, (48):759–74, 1988.

Piazza, Alberts, Hixson, Paranka, Li, Finn, Bogert, Guillen, Brendel, Gross, Speri, Ritchie, Burt, Ellsworth, Ahnen, Pamukcu, "Sulindac sulfone inhibits azoxymethane-induced colon carcinogenesis in rats without reducing prostaglandin levels," *Cancer Res.*, (57):2909–2915, 1997a.

Piazza, Rahm, Krutzsch, Speri, Paranka, Gross, Brendel, Burt, Alberts, Pamukcu, Ahnen, "Antineoplastic drugs sulindac sulfide and sulfone inhibit cell growth by inducing apoptosis," *Cancer Res.*, (55):311 3116, 1995.

Piazza, Rahm, Finn, Fryer, Li, Stumen, Pamakcu, Ahnen, "Apoptosis primarily accounts for the growth-inhibitory properties of sulindac metabolites and involves a mechanism that is independent of cyclooxygenase inhibition, cell cycle arrest, and p53 induction," *Cancer Res.*, (57): 2452–2459, 1997b.

Pollard, Luckert, "Prevention and treatment of primary intestinal tumors in rats by piroxicam," *Cancer Res.*, 49:6471–6473, 1989.

Porter, Herrera-Omelas, Pera, Petrelli, Mittleman, "Polyamine biosynthetic activity in normal and neoplastic human colorectal tissue," *Cancer,* 60:1275–1281, 1987.

Rao, Rivenson, Simi, Zang, Kelloff, Steele, Reddy, "Chemoprevention of colon carcinogenesis by sulindac, a nonsteroidal anti-inflammatory agent," *Cancer Res.,* (55):1464 1472, 1995.

Reddy, Maruyama, Kelloff, "Dose-related inhibition of colon carcinogenesis by dietary prioxicam, a nonsteroidal anti-inflammatory drug, during different stages of rat colon tumor development," *Cancer Res.,* 47:5340–5346, 1987.

Reddy, Sugie, "Effect of different levels of omega-3 and omega-6 fatty acids on azoxymethane-induced colon carcinogenesis in F344 rats," *Cancer Res.,* (48):6642–647, 1988.

Reddy, Nayini, Tokumo, Rigotty, Zang, Kelloff, "Chemoprevention of colon carcinogenesis by concurrent administration of piroxicam, a nonsteroidal anti-inflammatory drug with D,L-α-difluoromethylornithine, and ornithine decarboyxlase inhibitor, in diet," *Cancer Res.,* (50): 2562–2568, 1990.

Ritland, Gendler, "Chemoprevention of intestinal adenomas in the ApcMin mouse by piroxicam: kinetics, strain effects and resistance to chemosuppression." *Carcinogenesis* 20(1): 51–8, 1999.

Rousset, "The human colon carcinoma cell lines HT-29 and Caco-2: two in vitro models for the study of intestinal differentiation," *Biochimie,* (68):1035–1040, 1986.

Russell, Rosenau, Lee, "Cytolysis induced by human lumphotoxin. Cinemicrographic and electron microscopic observations," *Amer. J Pathol.,* 69:103–118, 1972.

Samaha, Asher, Payne, Garewal, Sampliner, Berstein, "Evaluation of cell ceath in EBV-transformed lymphocytes using agarose gel electrophoresis, light microscopy and electron microscopy. I. Induction of classic apoptosis by the bile salt, sodium deoxycholate," *Leukemia Lymphoma,* 19:95–105, 1995.

Samaha, Bernstein, Payne, Garewal, Sampliner, Berstein, "Bile salts induce apoptosis in goblet cells of the normal human colonic ucosa: relevance to colon cancer patients," *Acta Microscopica,* 4:43–58, 1995.

Samaha, Kelloff, Steele, Rao, Reddy, "Modulation of apopotsosi by sulindac, curcumin, phenylethyl-3-methylcaffeate, and 6-phenylhexyl isothiocyanate, apoptotic index as a biomarker in colon cancer chemoprevention and promotion," *Cancer Res.,* (57): 1301–1305, 1997.

Sanderson, "The mechanism of lymphocyte-mediated cytotoxicity," *Biol. Rev.,* 56:153–197, 1981.

Searle, Kerr, Bishop, "Necrosis and apoptosis: distinct modes of cell death with fundamentally different significance," *Pathol. Annual.,* 17:229–259, 1982.

Shiff, Koutsos, Qiao, Rigas, "Nonsteroidal antiinflammatory drugs inhibit the proliferation of colon adenocarcinoma cells: effects on cell cycle and apoptosis," *Esp. Cell. Res.,* 222:179–188, 1996.

Shiff, Qiao, Tsai, Rigas, "Sulindac sulfide, an aspirin-like compound, inhibits proliferation, causes cell cycle quiescence, and induces apoptosis in HT-29 colon adenocarcinoma cells," *J Clin. Invest.,* 96:491–503, 1995.

Shirasawa, Furuse, Yokoyama, Sasazuki, "Altered growth of human colon cancer cell lines disrupted at activated Ki-ras," *Science* (260):65–88, 1993.

Singh and Reddy, "Molecular markers in chemoprevention of colon cancer. Inhibition of expression of ras-p21 and p53 by sulindac during azoxymethane-induced colon carcinogenesis," *Annals of the New York Academy of Sciences,* (768):205–209, 1995.

Singh, Kelloft Reddy, "Intermediate biomarkers of colon cancer, modulation of expression of reas oncogene by chemopreventive agents during azoxymethane induced colon carcinogenesis," *Carcinogenesis,* (14):669–704, 1993.

Singh, Kulkarni, Kelloff, Reddy, "Modulation of azoxymethane-induced mutational activation of ras protooncogenes by chemopreventive agents in colon carcinogenesis," *Carcinogenesis,* (15): 1317–1323, 1994.

Singh, and Lippman, "Cancer chemoprevention. Part 2: Hormones, nonclassic antioxidant natural agents, NSAIDs, and other agents." *Oncology (Huntingt)* 12(12): 1787–800; discussion 1802, 1805, 1998.

Su, Kinzler, Vogelstein, Preisinger, Moser, Luongo, Gould, Dove, "Multiple intestinal neoplasia caused by a mutation in the murine homolog of the APC gene," *Science,* (256):668–670, 1992.

Strater, Koretx, Gunthert, Moller, "In situ detection of enterocytic apoptosis in normal colonic mucosa and in familial adenomatous polyposis," *Gut,* 37:819–825, 1995.

Tempero, Nishioka, Knott, Zetterman, "Chemoprevention of mouse colon tumors with difluromethylornithine during and after carcinogen treatment," *Cancer Res.,* (49): 5793–5797, 1989.

Thompson, Meeker, Herbst, Ronan, Minocha, "Effect of concentration of D,L-2-difluromethylornithine on murine mammary carcinogenesis," *Cancer Res,* (45):1170–3, 1985.

Thompson, Briggs, Paranka, Piazza, Brendel, Gross, Speri, Pamucku, Ahnen, "Inhibition of mammary carcinogenesis by sulfone metabolite of sulindac," *J. Nat'l Cancer Inst.,* (87):125–1260, 1995.

Thun, Namboodiri, Calle, Flanders, Heath, "Aspirin use and the risk of fatal cancer," *Cancer Res,* 53(6): 1322–7, 1998.

Trainer, Kline, McCabe, Faucette, Field, Chaikin, Anzano, Rieman, Hoffstien, Li, Gennaro, Buscarino, Lynch, Poste, Grieg, "Biological characterization and oncogene expression in human colorectal carcinoma cell lines," *Int. J. Cancer,* (41):287–296, 1988.

Vane, and Botting, "Mechanism of action of aspirin-like drugs," *Sem. in Arthritis and Rheumatism,* (26):2–10, 1997.

Vivona, Shpitz, Medline, Bruce, Hay, Ward, Stem, Gallinger, "K-ras mutations in aberrant crypt foci, adenomas and adenocarcinomas during azoxymethane-induced colon carcinogenesis," *Carcinogenesis*14(9): 1777–81, 1993.

Vogelstein, Fearon, Hamilton, "Genetic alterations during colorectal tumor development," *N. Engl. J. Med.*, (319): 525–532, 1988.

Voytesek, Bartek, Midglely, Lane, "An immunochemical analysis of the human nuclear phosphoprotein-53. New monoclonal antibodies and epitope mapping using recombinant p53," *J. Immunol. Methods,* 151:237–244, 1992.

Walker, Harmon, Glove, Kerr, "Patterns of cell death," *Meth. Archiev. Exp. Pathol.,* 13:18–54, 1988.

Ward, Todd, Santiago, O'Connor, Hawkins, "Activation of the K-ras oncogene in colorectal neoplasms is associated with decreased apoptosis," *Cancer,* (79): 110–1113, 1997.

Weeks, Herrmann, Nelson, Slaga, "α-Diflouromethylornithine, an irreversible inhibitor of ornithine decarboxylase, inhibits tumor promoter-induced polyamine accumulation and carcinogenesis in mouse skin," *Proc. Nat'l Acad. Sci. U.S.A.,* (79):6028–32, 1982.

Wechter, Kantoci, Murray, Quiggle, Leipold, Gibson, McCracken, "R-flurbiprofen chemoprevention and treatment of intestinal adenomas in the APC(Min)/+ mouse model: implications for prophylaxis and treatment of colon cancer." *Cancer Res,* 57 19:4316–24, 1997.

Winde, Lugering, Glodny, Schmid, Muller, Senninger, Osswald, "Decreased HER-2 tyrosine kinase expression in rectal mucosa of FAP patients following low-dose sulindac chemoprevention." *Cancer Lett,* 134(2): 201–7, 1998.

Wyllie, "Cell death: a new classification separation apoptosis from necrosis," *In: cell death in biology and pathology,* Bowen and Lockshin (eds), Chapman and Hall, New York, N.Y., 9–34, 1981.

Xu, Real, Welt, Schussler, Oettgen, Oettgen, Old, "Expression of TAG-72 in normal colon, transistional mucosa and colon cancer," *Int. J. Cancer,* 44:985–989, 1989.

Yang, Shamsuddin, "A new murine monoclonal antibody, CMU10, as a marker for colonic carcinoma and precancerous conditions," *Arch. Pathol. Lab. Med.,* 119:454–457, 1995.

What is claimed is:

1. A method for treating cancer in a patient comprising administering an effective amount of difluoromethylornithine (DFMO) in combination with the non-steroidal anti-inflammatory drug, celecoxib, to said patient, said cancer being susceptible to the combination of DFMO and celecoxib, wherein the combination of DFMO and celecoxib has an improved effect than either drug alone.

2. The method of claim 1, wherein celecoxib is administered at a dose of about 10 to 1000 mg/day.

3. The method of claim 1, wherein celecoxib is administered at a dose of about 10 to 500 mg/day.

4. The method of claim 1, wherein DFMO is administered at a dose of about 0.05 to about 5.0 gm/M$^2$/day.

5. The method of claim 1, wherein DFMO is administered at a dose of about 0.05 to about 0.50 gm/M$^2$/day.

6. The method of claim 1, wherein the cancer is colon cancer, breast cancer, pancreatic cancer, brain cancer, lung cancer, stomach cancer, a blood cancer, skin cancer, testicular cancer, prostate cancer, ovarian cancer, liver cancer, esophageal cancer.

7. The method of claim 6, wherein the cancer is colon cancer.

8. The method of claim 7, wherein the colon cancer is familial adenomatous polyposis.

9. The method of claim 1, wherein DFMO is administered prior to celecoxib.

10. The method of claim 1, wherein DFMO is administered after celecoxib.

11. The method of claim 1, wherein DFMO is administered at the same time as celecoxib.

12. The method of claim 1, wherein DFMO is administered at least a second time.

13. The method of claim 1, wherein celecoxib is administered at least a second time.

14. The method of claim 1, further comprising resection of a solid tumor.

15. The method of claim 14, wherein DFMO and celecoxib are administered prior to said resection.

16. The method of claim 14, wherein DFMO and celecoxib are administered after said resection.

17. The method of claim 1, wherein DFMO and celecoxib are administered directly to said tumor.

18. The method of claim 1, wherein DFMO and celecoxib are administered systemically.

19. The method of claim 1, wherein DFMO and celecoxib are administered into the regional vasculature of said tumor.

20. The method of claim 1, wherein DFMO and celecoxib are administered into the region lymph system of said tumor.

21. The method of claim 1, wherein DFMO and celecoxib are administered by different routes.

22. A method for preventing cancer in a patient in need thereof comprising administering an effective amount of difluoromethylornithine (DFMO) in combination with the non-steroidal anti-inflammatory drug, celecoxib, to said patient, said cancer being susceptible to the combination of DFMO and celecoxib, wherein the combination of DFMO and celecoxib has an improved effect than either drug alone.

23. A method for inhibiting the transition from a premalignant hyperproliferative condition to cancer in a patient comprising administering an effective amount of difluoromethylornithine (DFMO) in combination with the non-steroidal anti-inflammatory drug, celecoxib, to said patient, said cancer being susceptible to the combination of DFMO and celecoxib, wherein the combination of DFMO and celecoxib has an improved effect than either drug alone.

24. A method for inhibiting metastasis formation in a patient having cancer comprising administering an effective amount of difluoromethylornithine (DFMO) in combination with the non-steroidal anti-inflammatory drug, celecoxib, to said patient, said cancer being susceptible to the combination of DFMO and celecoxib, wherein the combination of DFMO and celecoxib has an improved effect than either drug alone.

* * * * *